(12) United States Patent
Calderoni

(10) Patent No.: US 7,804,599 B2
(45) Date of Patent: Sep. 28, 2010

(54) FLUID VOLUME VERIFICATION SYSTEM

(75) Inventor: Anthony Calderoni, Bristol, CT (US)

(73) Assignee: MGM Instruments, Inc., Hamden, CT (US)

( * ) Notice: Subject to any disclaimer, the term of this patent is extended or adjusted under 35 U.S.C. 154(b) by 288 days.

(21) Appl. No.: 12/220,634

(22) Filed: Jul. 24, 2008

(65) Prior Publication Data

US 2010/0023278 A1    Jan. 28, 2010

(51) Int. Cl.
*G01N 21/00* (2006.01)
*G01N 15/06* (2006.01)

(52) U.S. Cl. ..................... 356/445; 250/557

(58) Field of Classification Search ......... 356/432–442, 356/445–448; 250/577
See application file for complete search history.

(56) References Cited

U.S. PATENT DOCUMENTS

| | | | |
|---|---|---|---|
| 3,096,120 A | 7/1963 | Steiner et al. | |
| 3,756,078 A | 9/1973 | Yamasaki et al. | |
| 3,818,757 A | 6/1974 | Brown | |
| 3,935,735 A | 2/1976 | Lee | |
| 4,003,243 A | 1/1977 | Blu et al. | |
| 4,166,388 A | 9/1979 | Sun et al. | |
| 4,204,427 A | 5/1980 | Gothe et al. | |
| 4,208,909 A | 6/1980 | Maltby et al. | |
| 4,235,106 A | 11/1980 | Maltby et al. | |
| 4,326,851 A | 4/1982 | Bello et al. | |
| 4,341,736 A | 7/1982 | Drbal et al. | |
| 4,347,740 A | 9/1982 | Townsend | |
| 4,347,741 A | 9/1982 | Geiger | |
| 4,442,719 A | 4/1984 | Allen et al. | |
| 4,446,744 A | 5/1984 | Bearcroft | |
| 4,459,857 A | 7/1984 | Murray et al. | |
| 4,475,406 A | 10/1984 | Ansaldi et al. | |
| 4,499,640 A | 2/1985 | Brenton et al. | |
| 4,499,641 A | 2/1985 | Fleckenstein | |
| 4,515,015 A | 5/1985 | Kuhlman | |
| 4,536,711 A | 8/1985 | King et al. | |
| 4,551,785 A | 11/1985 | Kroner | |
| 4,589,077 A | 5/1986 | Pope | |
| 4,676,100 A | 6/1987 | Eichberger | |
| 4,739,492 A | 4/1988 | Cochran | |
| 4,778,451 A | 10/1988 | Kamen | |
| 4,790,378 A | 12/1988 | Montgonery et al. | |
| 4,850,805 A | 7/1989 | Madsen et al. | |
| 4,864,857 A | 9/1989 | Koon | |
| 4,970,468 A | 11/1990 | Ishizawa et al. | |
| 4,977,786 A | 12/1990 | Davis | |
| 4,988,975 A | 1/1991 | Nap | |
| 5,005,005 A * | 4/1991 | Brossia et al. | ............ 340/604 |
| 5,013,529 A | 5/1991 | Itoh | |
| 5,045,286 A | 9/1991 | Kitajima et al. | |
| 5,048,335 A | 9/1991 | Marsh et al. | |
| 5,049,878 A | 9/1991 | Stern | |
| 5,083,470 A | 1/1992 | Davis et al. | |
| 5,121,632 A | 6/1992 | Keeler et al. | |
| 5,212,992 A | 5/1993 | Calhoun et al. | |
| 5,245,873 A | 9/1993 | Fathauer et al. | |
| 5,304,347 A | 4/1994 | Mann et al. | |
| 5,311,769 A | 5/1994 | Hetzel | |
| 5,341,100 A | 8/1994 | Taylor | |

(Continued)

*Primary Examiner*—Michael P Stafira

(57) ABSTRACT

This invention describes a fluid transfer device which has a fluid handling system and a fluid detection system controlled by a central processing system which allows the device to accurately determine both the verification of fluid dispensed and the liquid level position in the reaction vessel.

11 Claims, 6 Drawing Sheets

U.S. PATENT DOCUMENTS

| | | |
|---|---|---|
| 5,365,783 A | 11/1994 | Zweifel |
| 5,428,997 A | 7/1995 | Paulsen |
| 5,443,791 A | 8/1995 | Cathcart et al. |
| 5,451,940 A | 9/1995 | Schneider et al. |
| 5,468,543 A | 11/1995 | Holt et al. |
| 5,493,922 A | 2/1996 | Ramey et al. |
| 5,495,130 A | 2/1996 | Schneider |
| 5,499,545 A | 3/1996 | Kimura et al. |
| 5,512,247 A | 4/1996 | Bonicina et al. |
| 5,529,754 A | 6/1996 | Bonicina et al. |
| 5,546,005 A | 8/1996 | Rauschwurger |
| 5,550,549 A | 8/1996 | Boger et al. |
| 5,554,937 A | 9/1996 | Sanders et al. |
| 5,559,339 A | 9/1996 | Domanik et al. |
| 5,582,797 A | 12/1996 | Meltzer |
| 5,600,997 A | 2/1997 | Kemp et al. |
| 5,610,527 A | 3/1997 | Yamaguchi |
| 5,611,420 A | 3/1997 | Hetzel |
| 5,612,227 A | 3/1997 | Inoue et al. |
| 5,639,426 A | 6/1997 | Kerr et al. |
| 5,648,727 A | 7/1997 | Nyberg et al. |
| 5,662,388 A | 9/1997 | Wuerth et al. |
| 5,665,601 A | 9/1997 | Kilmer |
| 5,672,050 A | 9/1997 | Webber et al. |
| 5,675,259 A | 10/1997 | Arndt et al. |
| 5,715,786 A | 2/1998 | Seiberth |
| 5,739,598 A | 4/1998 | Zatler et al. |
| 5,750,881 A | 5/1998 | Dorenkott et al. |
| 5,814,275 A | 9/1998 | Lewis et al. |
| 5,831,268 A * | 11/1998 | Morita et al. ............. 250/341.8 |
| 5,843,378 A | 12/1998 | El-Hage et al. |
| 5,855,851 A | 1/1999 | Matsubara et al. |
| 5,919,706 A | 7/1999 | Tajima |
| 5,973,415 A | 10/1999 | Brenner et al. |
| 6,016,697 A | 1/2000 | McCulloch et al. |
| 6,060,320 A | 5/2000 | Dorenkott et al. |
| 6,062,091 A | 5/2000 | Baumoel |
| 6,073,488 A | 6/2000 | Byatt et al. |
| 6,100,094 A | 8/2000 | Tajima |
| 6,121,049 A | 9/2000 | Dorenkott et al. |
| 6,148,666 A | 11/2000 | Roesicke |
| 6,158,269 A | 12/2000 | Dorenkott et al. |
| 6,161,956 A | 12/2000 | Jerkel |
| 6,283,719 B1 | 9/2001 | Frantz et al. |
| 6,478,547 B1 | 11/2002 | Savard et al. |
| 6,490,920 B1 | 12/2002 | Netzer |
| 6,551,558 B1 | 4/2003 | Mann et al. |
| 6,661,504 B2 * | 12/2003 | Rakucewicz ................ 356/128 |
| 6,851,453 B2 | 2/2005 | Lipscomb et al. |
| 6,851,663 B2 | 2/2005 | Satterfield |
| 6,914,555 B2 | 7/2005 | Lipscomb et al. |
| 7,259,712 B1 * | 8/2007 | McKeen et al. ............. 342/124 |
| 2003/0209093 A1 | 11/2003 | Lipscomb et al. |

* cited by examiner

FLUID VOLUME VERIFICATION SYSTEM

This Invention is a method and system for verifying the amount of fluid dispensed into a receptacle through a fluid delivery tube and/or for detecting a fluid surface within a container that is entered via the fluid delivery tube.

Automated analyzers are commonly used by clinical laboratories and by health science researchers to assay and determine inter alia the presence or amount of a particular analyte or group thereof in a biological sample. Typical biological samples for such assays include blood, urine, cerebrospinal fluid, sputum, stool, plants, water and soil. Analytes usually targeted in biological samples include antibodies, antigens, nucleic acids, toxins, and other chemical structures. Clinicians especially prefer automated analyzers over manual procedures because of their high throughput capabilities, reduced labor expenses, and the limits they place on human error that can lead to false or misleading results. To be most useful, an analyzer preferably automates the sample preparation and sample processing steps of an assay.

Sample preparation may be initiated by an automated fluid transfer system which transfers a fluid sample from a sample container to a reaction vessel for analysis. The automated fluid transfer system may also be used to transfer one or more assay reagents from their respective containers or associated reservoirs into the sample holding reaction vessel. After conducting the appropriate sample processing steps for a given assay, the contents of the reaction vessel may be examined by the automated analyzer to determine the amount or presence of at least one specific analyte. Detecting a targeted analyte in the sample might provide an indication that a particular pathogenic organism is present in the sample, or it might indicate a specific disease condition or state useful for determining or adapting a treatment regimen.

The fluid transfer system typically includes a fluid delivery probe operatively carried on a robotically controlled arm to perform aspiration and dispensing functions required for the fluid transfer process and pump coupled to the probe by a conduit system. During a fluid transfer operation, the robotic arm, under the control or command of a system controller, positions the fluid delivery probe above a sample or reagent container and moves the probe into the container until the tip of the probe reaches the fluid surface in the container. It is desirable that the distal tip of the probe be maintained right at or slightly below the fluid surface to avoid ingesting air into the probe during aspiration and to avoid possible cross-contamination that can occur if the probe is unnecessarily submerged into the fluid and fluid residue is carried on the exterior of the probe from one sample to another. Accordingly, a desired feature of an automated fluid delivery probe is a means by which contact of the probe tip with the fluid surface can be detected as the probe is being lowered into a fluid containing vessel. Once the fluid surface height is detected the fluid volume can be computed because the other dimensions of the vessel are known.

With the probe tip remained at the fluid surface, a pump, such as a syringe type pump, is activated to draw an amount sample or reagent fluid from the container into the probe. The amount of fluid aspirated will correspond to the volume and number of aliquots to be dispersed from the probe. The fluid delivery probe is thereafter moved into a position above a reaction vessel and a precise aliquot of fluid is dispersed. To insure that accurate results are obtained in the tests, a predetermined volume of the sample must be accurately aspirated and dispensed into the reaction vessel. Accordingly, another desirable feature of an automated fluid delivery probe is automated verification of fluid dispersed from the tube.

Different devices and methods for automatically determining when a probe tip has contacted a fluid surface in a container have been proposed in the available literature. For example, some surface detection operate on the basis of capacitance. The probe, if made from a conductive, e.g. a metal, conduit or conductive plastic will exhibit a finite amount of electrical capacitance to ground through the air. When the probe tip contacts a fluid surface, the higher or lower dielectric constant and greater surface area of the fluid results in a small, but measurable, increase or decrease in the capacitance of the probe.

Other surface detection mechanisms for incorporation onto a fluid delivery probe include two or more electrodes which may compromise tubular elements arranged coaxially with each other (eg. U.S. Pat. Nos. 5,304,347 and 5,550,059) or elongated conductors extending along the length of the probe and arranged in a spaced, parallel relationship (see eg. U.S. Pat. Nos. 5,045,286, and 5,843,378). When the probe contacts a fluid surface, the fluid, which contacts both electrodes simultaneously, electrically couples the electrodes to each other. If a voltage is applied across the electrodes the electrical coupling caused by the electrodes contacting the fluid surface results in a measurable change in the impedance across the electrodes.

U.S. Pat. Nos. 5,013,529 and 5,665,601 describe surface detection devices which incorporate a pressure sensor connected to a fluid line through which constant pressure gas is expelled through the tip of the probe. When the tip contacts the fluid surface, thereby blocking the gas emitting orifice (i.e. the end opening of the probe, a measureable change in the pressure is exhibited. U.S. Pat. No. 6,100,094 describes a surface detection device which includes an optic emitter which emits light axially through, or alongside, a tip. The light is reflected from the fluid surface back into the tip to a light sensor disposed within the tip. The amount of light reflected back to the light sensor detectably changes when the tip contacts the fluid surface.

The prior art surface detection sensors described above each suffer from certain shortcomings. For example achieving adequate accuracy and repeatability with capacitive surface sensors can be difficult because the change in capacitance exhibited when a probe contacts a fluid surface can be very small and thus difficult to detect. This is especially true where the fluid is a non-conductive fluid with a high dielectric value such as oil. Furthermore, because of the small capacitance changes exhibited, capacitive surface detection sensors can be susceptible to inaccuracies due to fluctuating stray capacitances caused by adjacent moving structures or changes in the amount of fluid contained in the probe and or container.

Dual electrode surface detection devices constructed to date, with side by side or coaxial arrangement of the electrodes, are complex and cumbersome. Surface detection devices that emit constant pressure gas can cause disturbances and even bubbling and/or atomization of the fluid. The effectiveness of optic sensors can be diminished due to residue or other buildup on the optic emitter and/or receiver.

Other devices and methods are described in the available literature for verifying aspiration and/or delivery of a fluid from the probe. For example, U.S. Pat. No. 6,121,049 describes a system wherein the pressure needed to hold up a column of aspirated fluid in the probe can be measured and compared to a predetermined standard to determine if a proper amount of fluid has been aspirated. By verifying a proper aspiration, a proper subsequent fluid delivery can theoretically be inferred U.S. Pat. No. 5,559,339 describes a system which includes Reflective Optical Sensors, each with an emitter-receiver pair, disposed adjacent to the pipette tip. Fluid flowing from the tip breaks the electromagnetic beam between the emitter and receiver, thereby indicating the flow of fluid. The duration of fluid flow can be monitored to determine if a proper amount of fluid has been dispensed.

Such fluid flow verification devices suffer from problems which can limit their usefulness. Pressure sensors that measure the amount of pressure required to hold up a column of aspirated fluid may be effective for confirming a proper aspiration of fluid, but, because fluid delivery can be interrupted by system leaks or occlusions blocking the probe, such sensors do not necessarily provide proof of proper fluid delivery. Also such devices are useful for fluid delivery procedures that involve aspiration of fluid into the probe prior to delivery from the probe into a reaction vessel. Such devices will not provide confirming information for fluid transfer systems in which fluid is pumped directly from a reservoir through a fluid delivery probe and into a reaction vessel without first being aspirated from another container.

As with surface detection devices that employ optic emitters and receivers, the effectiveness of the optic emitters and receivers, the effectiveness of the optic sensors employed to verify the fluid flow can be diminished by residual build up or other debris interfering with the emission or reception of the electromagnetic beam.

Therefore the devices and methods described previously in the prior art are susceptible to further improvement. Moreover, although surface detection and fluid delivery verification are important features of a consistently accurate automated fluid delivery probe, the prior art does not describe a simple, effective and accurate method and device for providing the combined capabilities of surface detection and fluid delivery verification in a single fluid delivery probe. Finally, the prior art does not describe a fluid delivery verification method or device in which the secondary, redundant means are employed for verifying fluid delivery to guard against erroneous indications of proper fluid delivery.

SUMMARY OF THE INVENTION

The present invention overcomes the shortcomings of and offers improvements over surface detection and fluid delivery verification systems described above.

This turbulence detection system is designed to confirm the dispensing of fluids into reaction vessels. Secondly, this invention can detect the liquid level in the vessel when the probe touches the liquid surface. It detects the turbulence of the fluid being injected along with the knowledge of the exact times that the pipettor is dispensing the fluid and combines those two independent but simultaneous observations together to verify the dispense of liquid. It combines probe height information obtained by a shaft encoder or like device with the disturbance of the liquid level by a probe to determine the liquid volume.

DETAILED DESCRIPTION OF THE PREFERRED EMBODIMENT

The robotic substance transfer device 10 can be of any configuration required by the overall instrument of which it is a part. The description below is for a device composed of 100 test tubes but anyone skilled in the art could configure it for any number of receivers and of any size or shape as long as they are made of a transparent substance.

Figure 1:
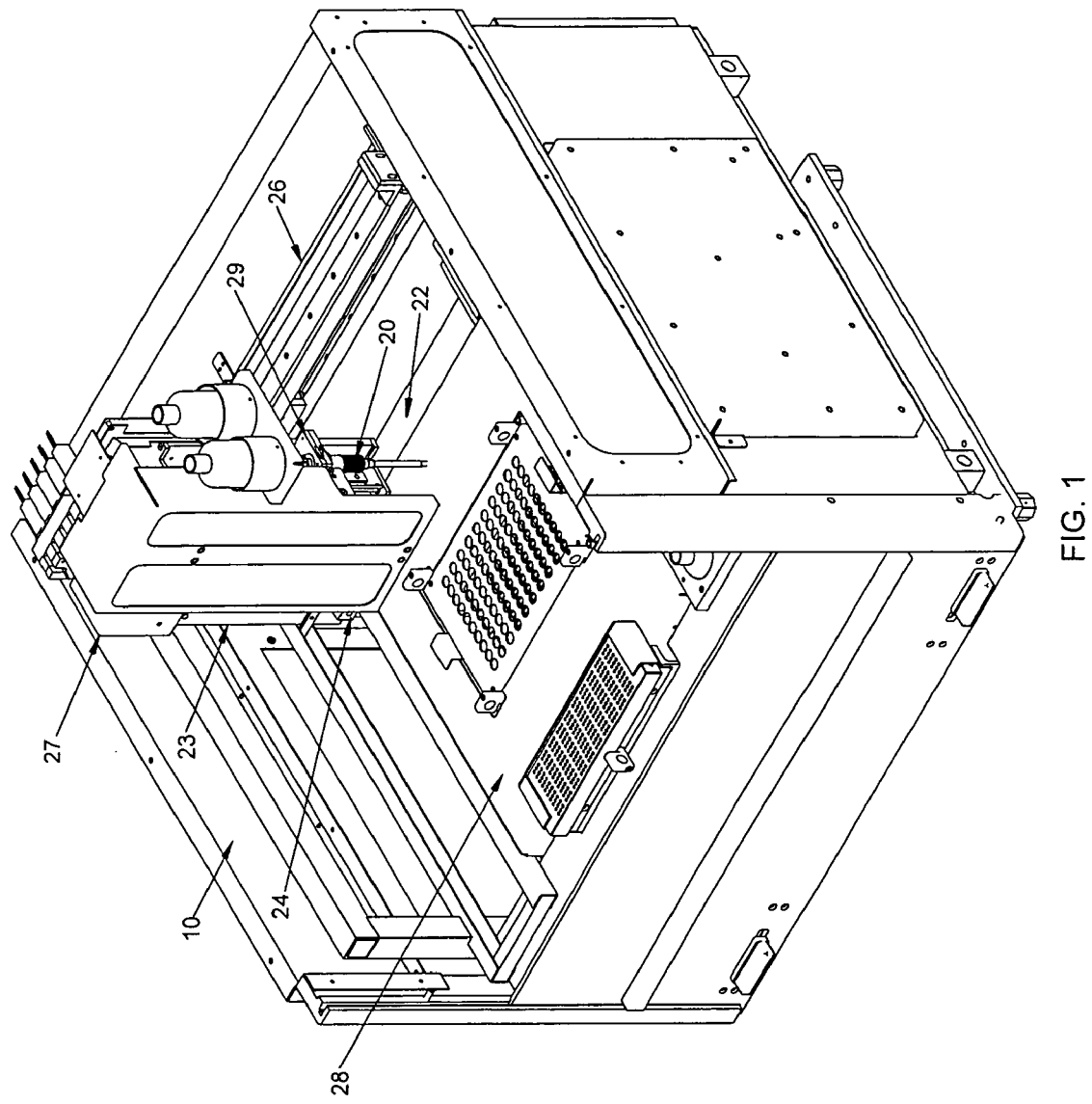
FIG. 1 is a Perspective View of a Robotic Substance transfer system.

As shown in FIG. 1 the robotic substance transfer mechanism contains a fluid delivery probe 20, has a fluid delivery conduit assembly 22 or disposable tip which is in turn mounted on a gantry assembly 23 which provides X-Y motion in a horizontal plane and Z motion in a vertical plane. The fluid delivery probe 20 is mounted on a lateral translation boom 26 which in turn is mounted on and supported by a longitudinal translation boom 24 as seen in the figure. The X-Y motion in the horizontal plane can be effected by motors placed within a housing 27 for moving the fluid delivery probe 20 along the lateral boom 26. A translation motor which cannot be seen within the housing 28 powers a driving device which works with a track formed along the longitudinal translation boom 24 to move the housing 27 reciprocally along the longitudinal boom 24. Movement of the fluid delivery probe 20 along the lateral translation boom 26 may be effected by a motor within the housing 27 and coupled to, for example, an endless belt disposed within the lateral translation boom 26 and attached to the fluid delivery probe 20 or a lead screw as it rotates above its own axis. Another such motor not shown is carried on the substance transfer mechanism 29 along the lateral translation boom 26 and is coupled to the fluid delivery probe 20, for example, by a lead screw or a rack and pinion arrangement for effecting Z-axis, vertical movement of the fluid delivery probe 20.

Figure 2:
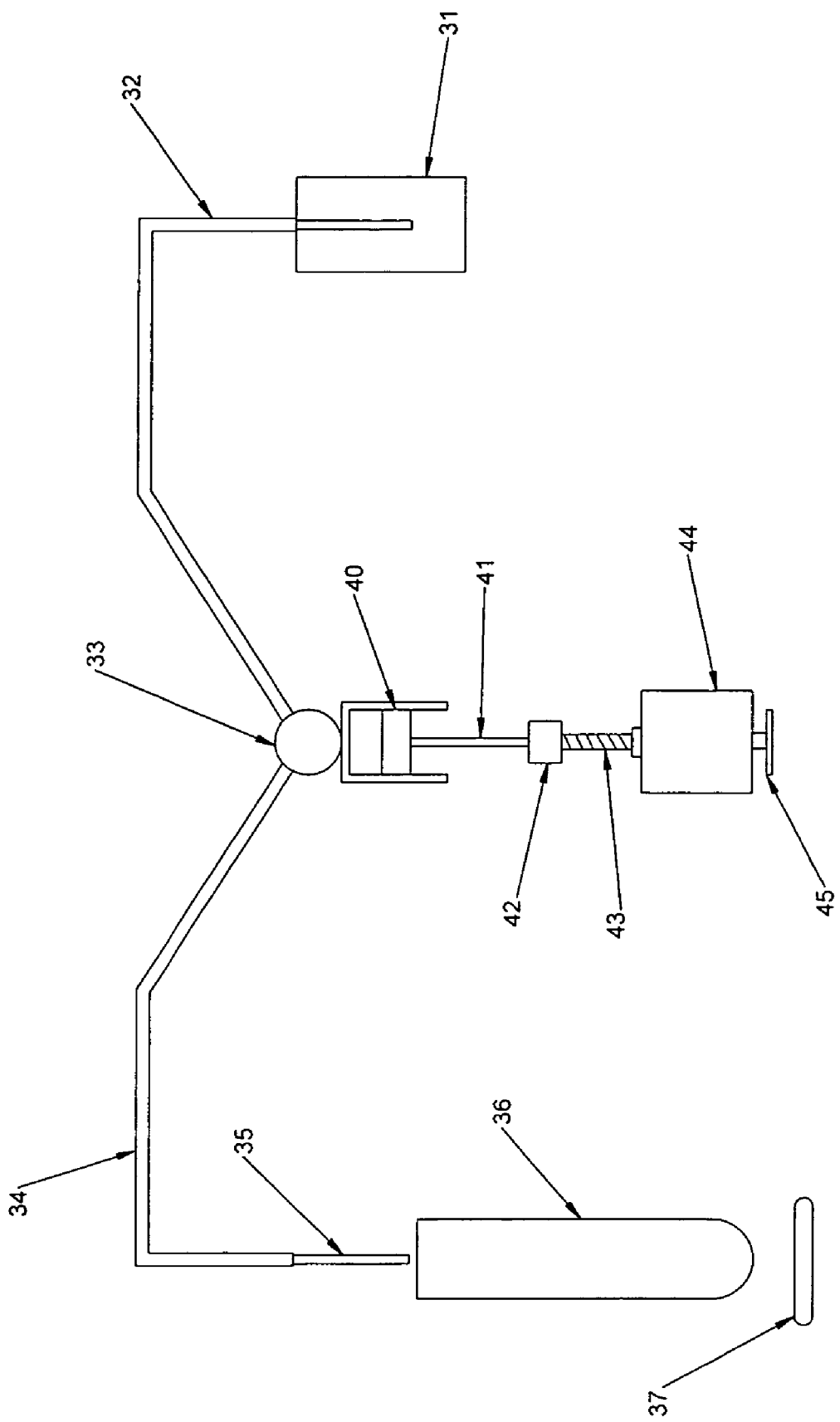
FIG. 2 shows the Pump Dispenser Mechanism which is embodied within a typical Substance Transfer Mechanism.

FIG. 2 describes the Pump Dispense Mechanism. A fluid reservoir 31 is connected by inert tubing 32 which can be flexible or rigid to one port of a 3-way fluid valve 33, A second port of that 3-way valve is connected to a mechanism which can extract a measured amount of fluid from the fluid reservoir 31 and then when necessary dispense that fluid to another portion of inert tubing 34 which is in turn connected to a Dispense Tip 35. This pipettor mechanism is mounted carefully above a reaction vessel 36, in this case a test tube which in turn is mounted above a reflective optical sensor 37. The reflective sensor provides both verification of fluid delivery as well as timed position detection of liquid level sense utilizing the shaft encoder 45 rotational information.

The third port of the 3-way fluid valve is attached the actual mechanism which controls the flow of the fluids from the reservoir to the reaction vessel. The 3-way valve 33 is directly connected to either a syringe or collapsible bellows 40 which in turn is connected to a piston 41, then to a nut 42 on top of a screw 43 which is driven by a motor 44 controlled by the electronic commands of the program, which in turn, is supplied with rotation information provided by shaft encoder 45.

Figure 3:
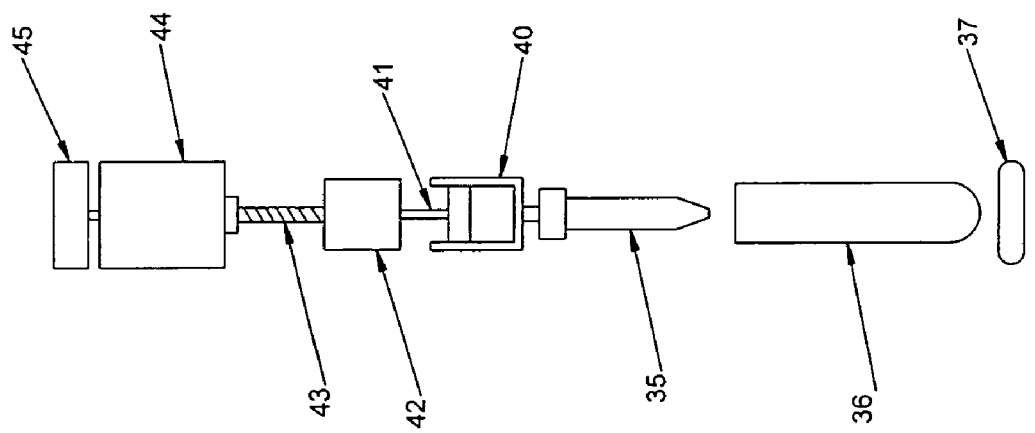
FIG. 3 shows the Pipettor Mechanism which is also imbedded within a typical Substance Transfer Mechanism

FIG. 3 offers another method of how the pipettor mechanism can deliver an exact amount of fluid from a reservoir to the reaction vessel 36. The fluid that was delivered is verified by the reflective optical sensor. To further enforce the integrity of the liquid measurements a disposable tip 35 is changed whenever the liquid in the reservoir is changed; changing the tip also prevents cross-contamination.

Figure 4:
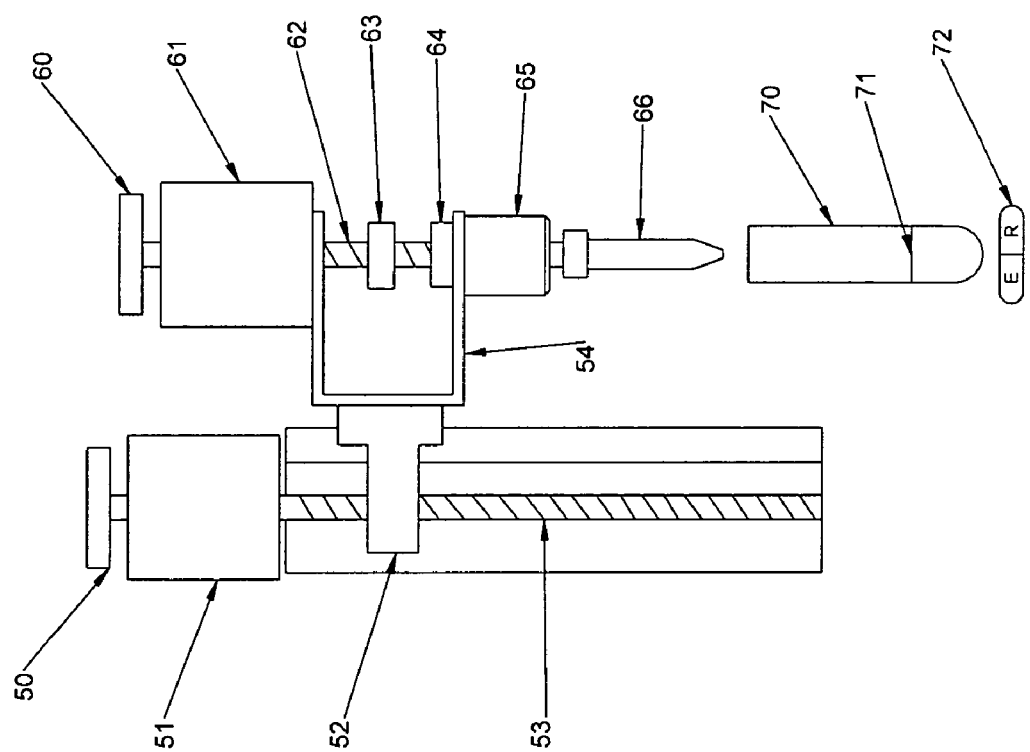
FIG. 4 presents a Perspective View of the Fluid Delivery System's Pipettor and Pipettor Elevator Mechanism.

FIG. 4 presents a Perspective View of the fluid delivery mechanism (pipettor) and the elevator which raises and lowers the pipettor into each sequential test tube.

The left portion illustrates the elevator which raises and lowers the pipettor into and out of the reaction vessel 70 to deliver the necessary liquid materials for a given determination. The shaft encoder 50 together with electronic commands of the program controls the elevator motor 51 which in turn rotates an elevator screw 53 through the nut and guide block 52. That nut and guide block is securely attached to or is part of a pipettor support 54 together with electronic controls of the program. A shaft encoder 60 atop the pipettor support 54 controls the pipettor motor 61 which is attached to a screw device 62 which passes through a nut 63 above a piston or actuator 64 which raises or lowers the bellows or syringe 65 to insert or extract fluid from the reaction vessel 70. This fluid delivery nozzle can have a reusable or disposable tip 66 which does not have to be conductive.

The liquid level 71 and the turbulence caused by the liquid dispensed into the reaction vessel is continuously monitored by means of the reflective optical sensor located directly below the reaction vessel. The letters E and R in the reflective optical sensor 72 indicates that this device contains an energy emitter and an energy receptor separated by an impermeable wall. Further, rotational information sent to the program by shaft encoder 59 taken together with reflection detection by sensor 72 when reusable or disposable tip 66 touches liquid level 71 defines the liquid level within the reaction tube 70.

Figure 5:
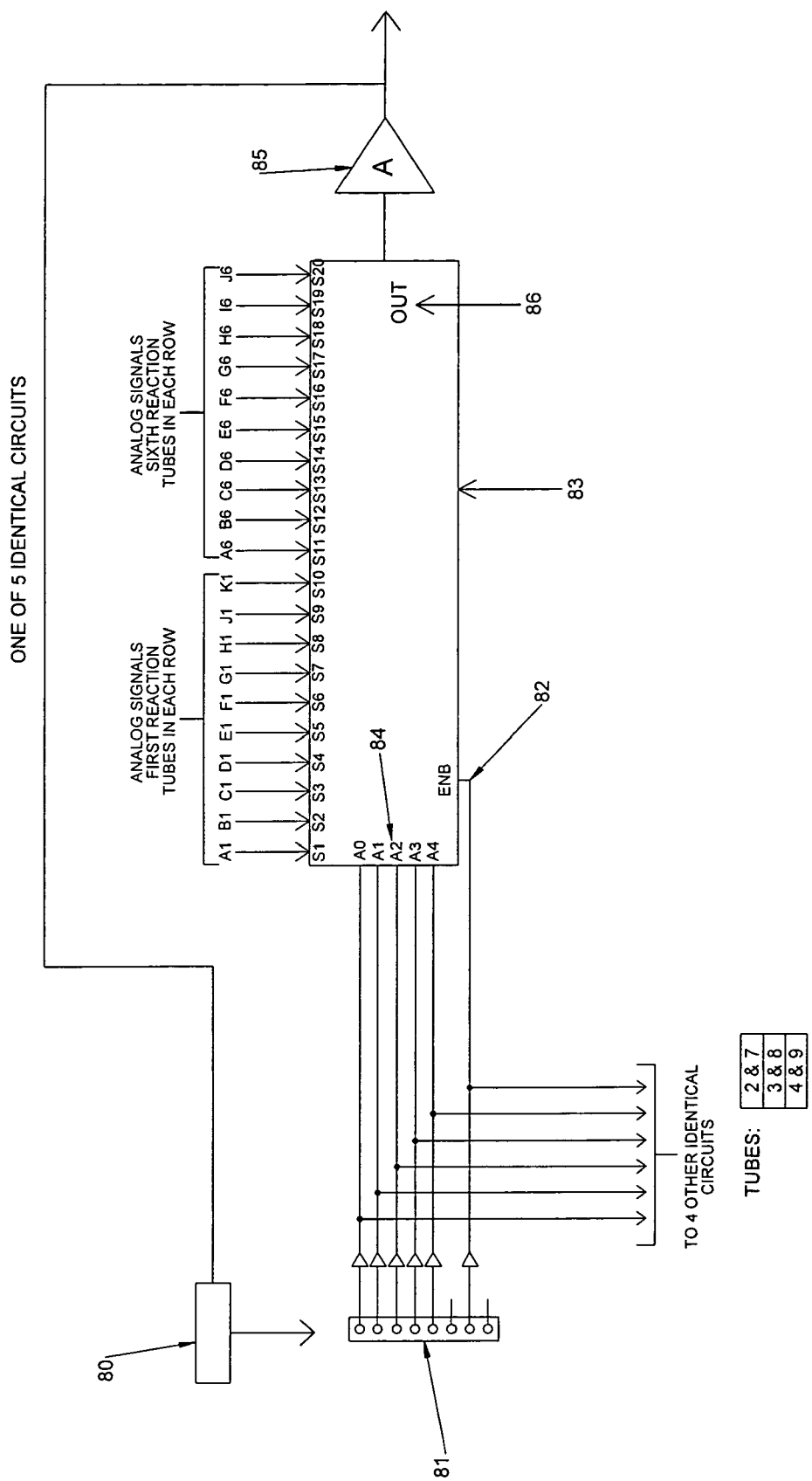
FIG. 5 one of the five identical circuits involved in processing the results of a 100 test tube determination device.

FIG. 5 shows one of five identical detector circuits each of which come into use as the pipettor mechanism moves from one to other and performs its function. It then proceeds to perform that function on the other 4 identical circuits for the remainder of the 5 groups of twenty tubes. A Central Processing Unit or controlling computer 80 of any type is connected to circuit array via a port 81 which then enables input 82 to proceed to the Multiplexer integrated circuit 83 which is connected to the 20 different optical sensor outputs. The address lines A0 through A4 84 select which one of the 20 optical sensors to be read during a given measurement cycle. The enable input 82 then connects that chosen optical sensor output to the out output line 80 of the multiplexer integrated circuit 83. Therefore the computer controls which optical sensor is to be monitored for possible liquid level detection or for the possible liquid verification as the case warrants. That output then passes to the amplifier filter discriminator 85 and the returns to the Central Processing Unit for recording.

Figure 6:
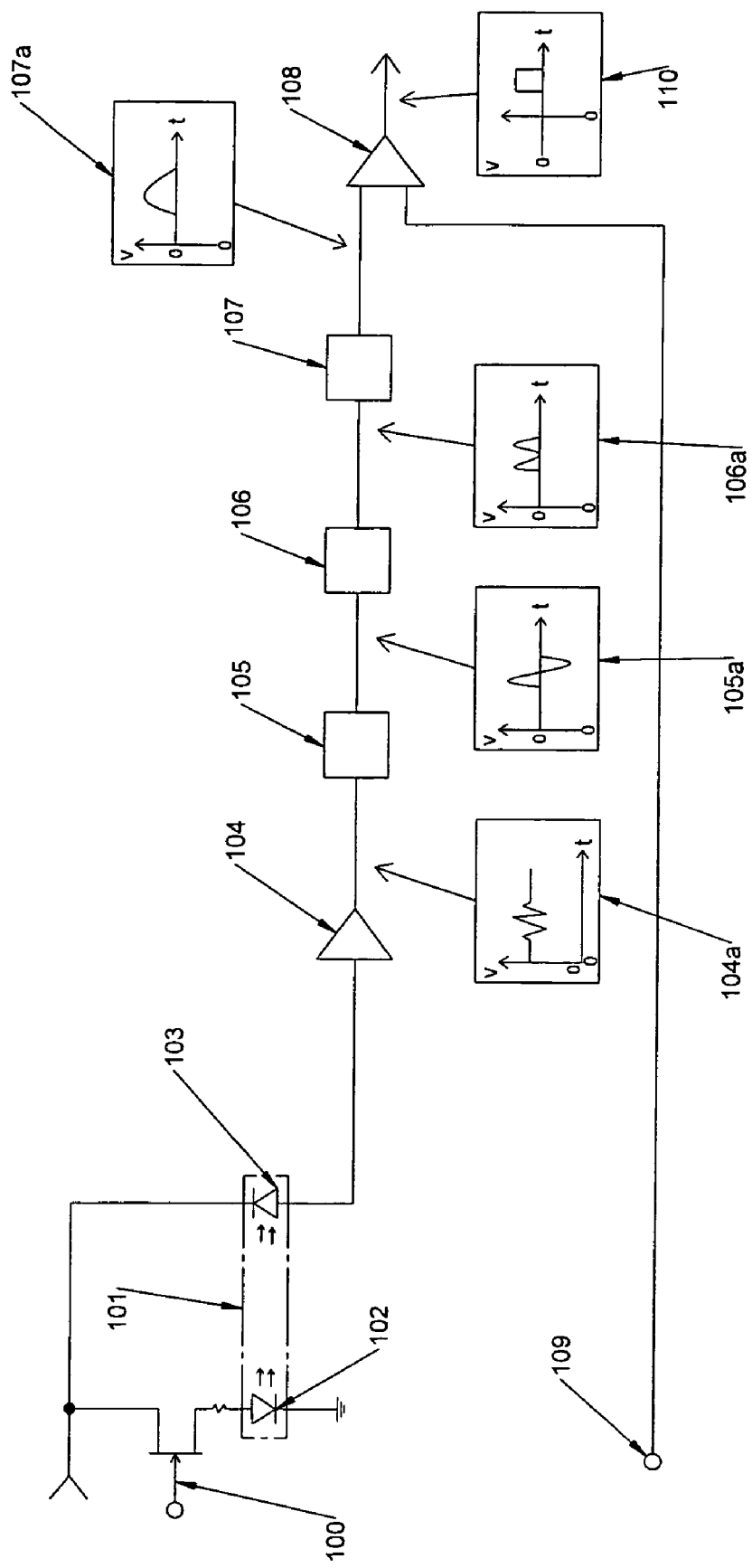
FIG. 6 shows the sensor circuit Block Diagram.

FIG. 6 presents a circuit block diagram of the circuits within amplifier filter discriminator 85 in FIG. 5. The tube select signal 100 enters the circuit at the point of the Optical Sensor Module 101. The signals from the optical emitter 102 that are reflected by the liquid level to the optical receiver 103 are passed to the high gain amplifier 104 which presents an output signal like 104a having both a steady (dc) part and a variable (ac) part and the signal goes through a band pass filter 105 which presents the modified signal 105a effectively removing the steady (dc) part of the signal then passes through a precision rectifier 106 which then outputs the rectified signal 106a. Next the rectified signal goes through a low pass envelope filter 107 giving the final signal 107a which enters the level comparator 108 to be compared with the signal coming from the variable threshold 109 produced by the control mechanism to present the final signal which verifies the liquid dispensed and/or the liquid level in the test tube 110.

The signal received by this method is free from any errors which could have been caused such problems as level variation cause by surface tension with an object, vibrations, waves in the liquid sample, build-up of material on surfaces and the like which are problems presented by the prior art.

As mentioned above, this invention has been described in terms of the most preferred format, but other formats including especially shape and size of the reaction vessel and other minor modifications that could be established by on skilled in the art.

What is claimed is:

1. A fluid transfer device comprising a fluid handling system and a fluid detection system wherein:

a fluid flow conduit which ends with a fluid delivery nozzle attached to a fluid movement device which is attached to a piston or actuator which in turn is attached to a screw or nut then attached to a pipettor motor having a shaft encoder controlled by a central processing unit all of which is held in place by a nut and guide block which in turn is mounted on an elevator screw of an elevator mechanism which has an elevator motor and its own shaft encoder controlled by the same central processing unit;

a transparent reaction vessel selected from an array of such reaction vessels designated by the central processing unit which vessel is firmly mounted above a reflective optical sensor having an emitter and receiver circuit separated by a non-transparent wall;

whereby the emitter circuit produces an optical signal or electromagnetic wave which is sent to the surface of the liquid in the reaction vessel and is altered by the liquid surface position and turbulence or liquid surface variations and reflected to the receiver circuit thus allowing the central processing unit to accurately determine both the verification of fluid dispensed and the liquid level position within the reaction vessel.

2. The device of claim 1 where the fluid delivery nozzle is conductive.

3. The device of claim 1 where the fluid delivery nozzle is non-conductive.

4. The device of claim 1 where the fluid movement is accomplished by a piston.

5. The device of claim 1 where the fluid movement is accomplished by an actuator.

6. The device of claim 1 where the central processing unit is a conventional computer.

7. The device of claim 1 where the central processing unit is a microprocessor.

8. The device of claim 1 where the reaction vessel is a test tube.

9. The device of claim 1 where the reaction vessel is a beaker.

10. The device of claim 1 where the reaction vessel is a bottle.

11. A device of claim 1 where the emitter circuit of the reflective optical sensor is an optical signal which can be detected and collected by the optical receiver and further transmitted to the central processing unit to determine the verification of fluid dispensed and the liquid level then within the reaction vessel.

* * * * *